United States Patent [19]

Winstrom

[11] Patent Number: 4,800,883
[45] Date of Patent: Jan. 31, 1989

[54] APPARATUS FOR GENERATING MULTIPHASIC DEFIBRILLATION PULSE WAVEFORM

[75] Inventor: William L. Winstrom, Andover, N.J.

[73] Assignee: Intermedics, Inc., Angleton, Tex.

[21] Appl. No.: 847,283

[22] Filed: Apr. 2, 1986

[51] Int. Cl.$^4$ .............................................. A61N 1/36
[52] U.S. Cl. ............................................... 128/419 D
[58] Field of Search ..................................... 128/419 D

[56] References Cited

U.S. PATENT DOCUMENTS

| | | | |
|---|---|---|---|
| 3,093,136 | 6/1963 | Lohr | 128/423 |
| 3,211,154 | 10/1965 | Becker et al. | 128/419 D |
| 3,241,555 | 3/1966 | Caywood et al. | 128/421 |
| 3,359,984 | 12/1967 | Daniher et al. | 128/419 |
| 3,513,850 | 5/1970 | Weber | 128/419 D |
| 3,563,247 | 2/1971 | Bowers | 128/422 |
| 3,605,754 | 9/1971 | Jaros et al. | 128/419 D |
| 3,614,954 | 10/1971 | Mirowski et al. | 128/419 D |
| 3,805,795 | 4/1974 | Denniston et al. | 128/419 D |
| 3,924,641 | 12/1975 | Weiss | 128/419 PG |
| 3,946,745 | 3/1976 | Hsiang-Lai et al. | 128/421 |
| 3,952,750 | 4/1976 | Mirowski et al. | 128/419 D |
| 4,210,149 | 7/1980 | Heilman et al. | 128/419 D |
| 4,402,322 | 9/1983 | Duggan | 128/419 PG |
| 4,637,397 | 1/1987 | Jones et al. | 128/419 D |

OTHER PUBLICATIONS

Schuder et al., "Medical & Biological Engineering & Computing" vol. 20, No. 4, Jul. 1982, pp. 419–424.
Schuder, Difibrillation of 100 kg Calves with Asymmetrical, Bidirectional, Rectangular Pulses, Cardiovascular Research 419–426 (1984).
Jones, Decreased Difibrillator-Induced Dysfunction with Biphasic Rectangular Waveforms, Am. J. Physiol. 247 (Heart Circ. Physiol. 16): H792–H796 (1984).

Primary Examiner—William E. Kamm
Attorney, Agent, or Firm—Russell J. Egan

[57] ABSTRACT

An apparatus suitable for use in an implantable automatic defibrillation system for automatically generating a multiphasic defibrillation pulse waveform in response to sensed fibrillation has first and second series charge-storing capacitors having a common terminal and two other terminals each at different potentials. A controller senses cardiac fibrillation and generates a control signal which causes a charging circuit to charge the capacitors to selected voltage levels in sequentially alternating charge generation and charge coupling cycles. A voltage level detector senses the stored voltage level, disables the charging circuit when the sensed voltage reaches a predetermined level, and informs the controller that the capacitors are fully charged. The controller then communicates control signals indicative of pulse magnitude, duration, and polarity to a multiphasic pulse generator having a number of high-power switches and corresponding switch drivers interposed in circuit between the heart and the terminals of the charge-storing capacitors. The drivers control the conduction states of the switches according to the control signals to establish selected circuit paths between the three terminals and the heart, and to thereby deliver to the heart a multiphasic waveform having pulses with the selected parameters of magnitude, duration, and polarity.

30 Claims, 7 Drawing Sheets

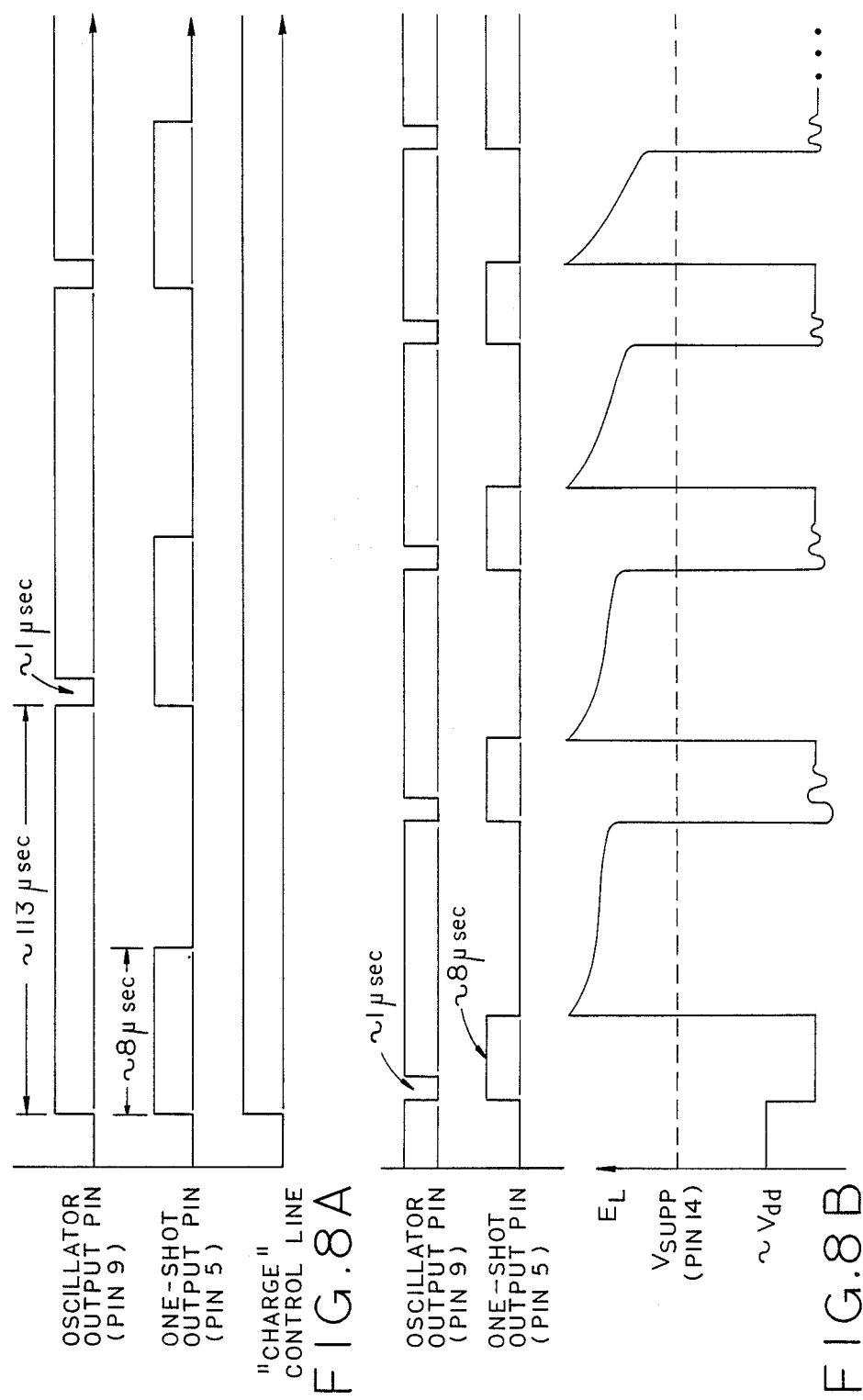

APPARATUS FOR GENERATING MULTIPHASIC DEFIBRILLATION PULSE WAVEFORM

BACKGROUND OF THE INVENTION

1. Field of the Invention

The invention disclosed herein relates generally to the field of heart defibrillator equipment. More specifically, the present invention relates to a special defibrillator apparatus which is suitable for use in implantable, automatic cardioversion systems, and which can generate particularly effective and beneficial high-voltage multiphasic defibrillation waveforms.

2. Description of the Prior Art

Ventricular fibrillation is almost always fatal unless promptly arrested. It has long been known that the application of a high energy pulse to the heart is often particularly effective in arresting this otherwise fatal condition and in restoring the synchronous operation of the heart muscles.

Automatic, implantable fibrillation sensors and defibrillation pulse generators are known in the art. See, for example, U.S. Pat. Nos. 3,614,954 and 3,614,955 to Mirowski et al., U.S. Pat. No. 4,254,775 to Langer, and U.S. Pat. No. 4,384,585 to Zipes. Such defibrillators, in order to be feasible, must occupy a minimal amount of space, be reliable in operation, and make efficient use of a depletable energy source.

It has been common for such prior art implantable defibrillators to generate unipolar type high-energy defibrillation pulses. See, for example, U.S. patent No. to Langer, U.S. Pat. No. Re. 30,387 to Denniston et al., U.S. Pat. No. Re. 30,372 to Mirowski et al., and U.S. Pat. No. 4,210,149 to Heilman et al. However, the use of unipolar pulses has been known to produce certain undesirable side effects including damage to the heart tissue near the electrode sites, induction of certain post-shock arrhythmias, and changes in the S-T segment. Moreover, under certain circumstances, such pulses are not effective to arrest ventricular fibrillation.

Recent medical research has shown that many of the problems associated with unipolar cardioverting pulses are alleviated or eliminated entirely when multiphasic cardioverting pulse trains are employed and that certain benefits are also obtained. For instance, it has been found that certain beneficial post-shock effects are imparted to the defibrillated heart by the trailing pulse of a three phase defibrillation waveform and that the effect vary with the level of energy imparted to the heart by this pulse. In addition, it has been found that the success rate in arresting ventricular fibrillation using three phase pulse waveforms is significantly greater than with unipolar pulses. See, for example, Schuder, *Defibrillation of 100 kg Calves With Asymmetrical, Bidirectional, Rectangular Pulses*, Cardiovascular Research 419–426 (1984), and Jones, *Decreased Defibrillator-Induced Dysfunction With Biphasic Rectangular Waveforms*, Am. J. Physiol. 247 (Heart Circ. Physiol. 16): H792-H796 (1984). Of course, many multiphasic waveform variations are possible and research is continuing in this area to discover others which may provide additional benefits and advantages in cardioverting and other applications.

A number of apparatuses for generating various forms of biphasic signals for pacing or defibrillation applications are known. One group of known apparatuses are manually-operated, electromechanical defibrillation pulse generators. These are not intended for and are totally unsuitable for use in automatic, implantable defibrillation systems, due to their size, mechanical nature, and high power requirements. See, for example, the biphasic defibrillation pulse generators described in U.S. Pat. Nos. 3,093,136 to Lohr, 3,241,555 to Caywod et al., and 3,359,984 to Daniher et al.

Another group of known apparatuses are biphasic pacing pulse generators such as those described in U.S. Pat. Nos. 3,924,641 to Weiss, 4,402,322 to Duggan, 3,563,247 to Bowers, and 3,946,745 to Hsiang-Lai et al. These known apparatuses have solved some of the problems of the electromechanical biphasic defibrillation pulse generators, but are not intended for and are not suitable for efficiently generating and applying to the heart the high-voltage pulses necessary to arrest ventricular fibrillation. In addition, the known pacing pulse generators lack the flexibility to generate the variety of multiphasic waveforms which medical research has recently shown to be advantageous in cardioversion applications, and to generate additional waveforms which continuing research may in the future discover to be beneficial. Moreover, these known generators provide no protection to the patient from internal malfunctions.

Accordingly, it is an object of the present invention to provide a highly energy efficient multiphasic pulse generator suitable for use in implantable automatic defibrillators.

It is another object to provide such a generator that is simple but flexible in its design and application and that can generate a variety of multiphasic waveforms.

It is still another object to provide a multiphasic defibrillation pulse generator that provides improved operational stability and accuracy independent of the magnitude of the pulses to be applied to the heart.

It is a further object to provide a multiphasic pulse generator that provides safeguards to the patient against internal malfunctions.

SUMMARY OF THE INVENTION

The above objects and attendant advantages are achieved by providing an apparatus which generates multiphasic defibrillation pulse waveforms having selected parameters of magnitude, polarity, and duration. The apparatus includes a charging circuit connected to a charge-storing circuit which provides at least three different output potentials. The charging circuit charges the chargestoring circuit to a selected charge level in response to a control signal indicative of fibrillation. An electrical conduction device conducts the output potentials to a heart. When the charge storing circuit is charged to a selected charge level, a multiphasic pulse generator selectively and sequentially connects and disconnects the conduction device and the output potentials to deliver to the heart a multiphasic defibrillation waveform having pulses with selected duration, magnitude, and polarity parameters.

The novel elements believed to be characteristic of the present invention are set forth in the appended claims. The invention itself, together with additional objects and attendant advantages, will best be understood by reference to the following detailed description, which, when taken in conjunction with the accompanying drawings, describes a presently preferred embodiment.

BRIEF DESCRIPTION OF THE DRAWINGS

An exemplary illustration of an apparatus for generating a multiphasic defibrillation pulse waveform comprising a presently preferred embodiment of the invention is contained in the appended drawings in which:

FIG. 8a is a timing diagram showing the relative timing of the oscillator output, one-shot output, and charge-control signal of the circuit of FIG. 3;

FIG. 8b is a timing diagram showing the relative timing of the oscillator output, the one-shot output, and the voltage $E_L$ at the drain of the power FET 24 in the circuit of FIG. 3.

DETAILED DESCRIPTION OF A PRESENTLY PREFERRED EMBODIMENT

Figure 1:
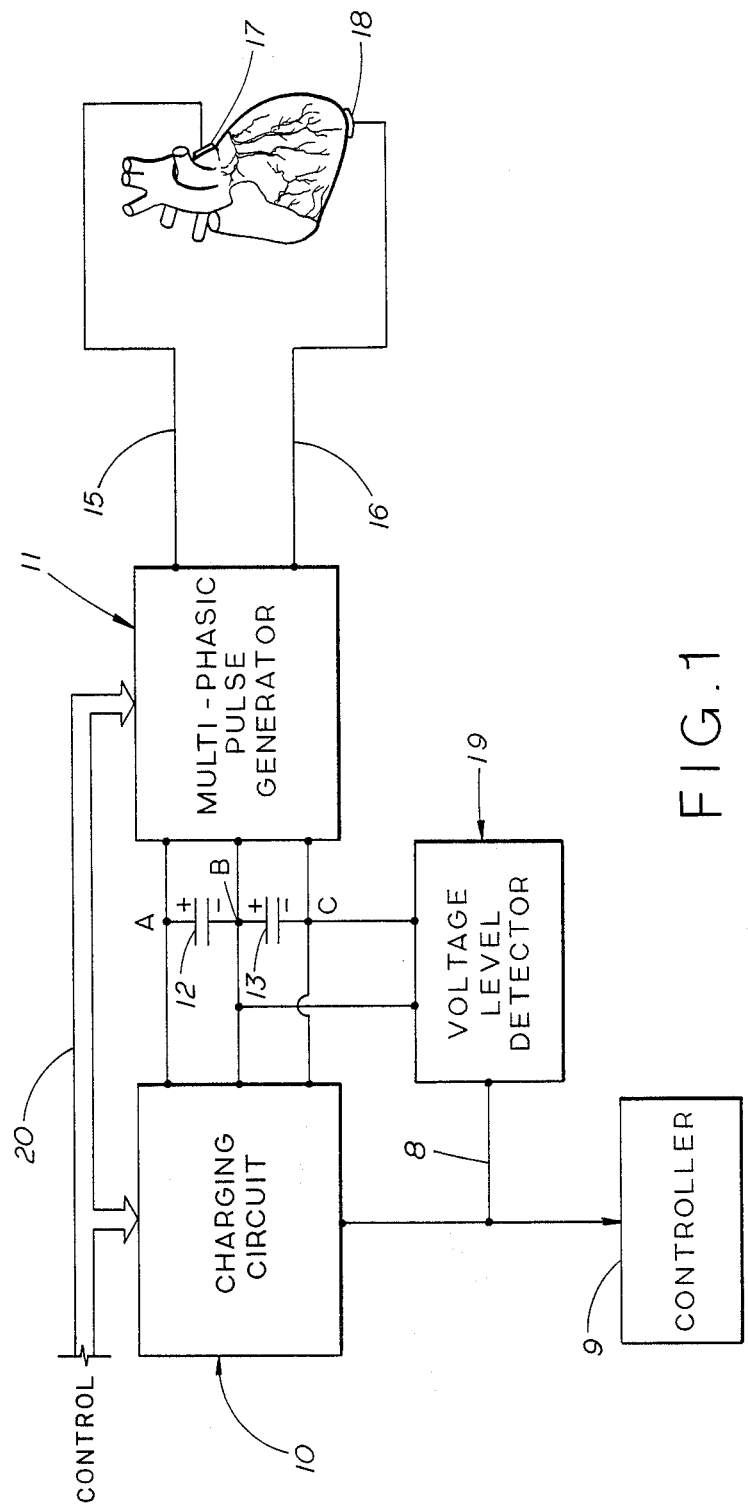
FIG. 1 is a general block diagram of the apparatus for generating a multiphasic defibrillation pulse shown with a heart.

FIG. 1 shows a block diagram of a multiphasic defibrillation pulse generator apparatus comprising a presently preferred embodiment of the invention. The apparatus comprises a charging circuit 10, a multiphasic pulse generator 11, and first and second high-voltage charge-storing series capacitors 12,13 positioned between the charging circuit 10 and multiphasic pulse generator 11 in parallel therewith and electrically interconnecting the two. The series connection of the charge-storing capacitors 12,13 establishes three terminals, A, B, and C, with terminal B being a common terminal, and each of the terminals having a different potential when the charge-storing capacitors 12,13 are charged. The multiphasic pulse generator 11 in turn electrically connects to the heart 14 via electrically conductive output and return leads 15,16. Leads 15,16 typically have first and second conductive patches 17,18, or other conductive connectors attached to their respective free ends for making electrical connection to the heart 14 in a manner and location known to those skilled in the art. A voltage level detector 19 is electrically connected across the second charge-storing series capacitor 13, and to the charging circuit 10. A controller 9 supplies control signals over control lines 20 to the charging circuit 10 and multiphasic pulse generator 11 to control their operation.

The first and second charge-storing capacitors 12,13 are suitably 350 microfarad aluminum electrolyte type capacitors such s those manufactured by Rubycon. The controller may be any conventional microprocessor or other digital or analog controller suitable for use in automatic, implantable devices. An example of such controller can be found in U.S. Pat. Nos. 4,390,022 and 4,404,972.

The construction and use of such controllers is well known to those skilled in the art and a description herein is not necessary to an understanding of the present invention.

The controller 9 senses when the heart 14 enters a state of fibrillation and in response generates a "charge enable" control signal. Many ways for sensing and determining fibrillation are known to those skilled in the art, and the controller suitably determines the condition of fibrillation in any such known manner. The "charge enable" signal is conducted by the control lines 20 to the charging circuit 10. In response, the charging circuit 10 very quickly (typically 6-7 seconds) charges the first and second charge-storing capacitors 12,13 to first and second preselected voltages. In the presently preferred embodiment, the capacitors 12,13 are simultaneously charged to equal voltages. The voltage level detector 19 determines when the first and second charge-storing capacitors 12,13 are charged to the preselected voltage levels and generates a "charge disable" control signal which is transmitted over line 8 both to the charging circuit 10 and to the controller 9. The controller then generates a series of control signals which are conducted by the control lines 20 to the multiphasic pulse generator 11. The biphasic pulse 11 is responsive to these control signals to electrically switch the output and return leads 15,16 into and out of contact with the terminals A, B, C of the charge-storing capacitors 12,13, thereby establishing selected discharge paths for the capacitors 12,13 through the heart 14. The polarities, durations, and magnitudes of the discharges are determined by the control signals.

After a first multiphasic defibrillation pulse waveform is delivered to the heart 14, the controller may again sense the heart's condition and initiate additional charging and defibrillation, if necessary. Preferably, the controller senses the electrical activity of the heart 14, and stores the number of defibrillation attempts. When no electrical activity is sensed, or when a predetermined number of unsuccessful defibrillation attempts have been made, the controller preferably does not initiate further defibrillation attempts.

Figure 2:
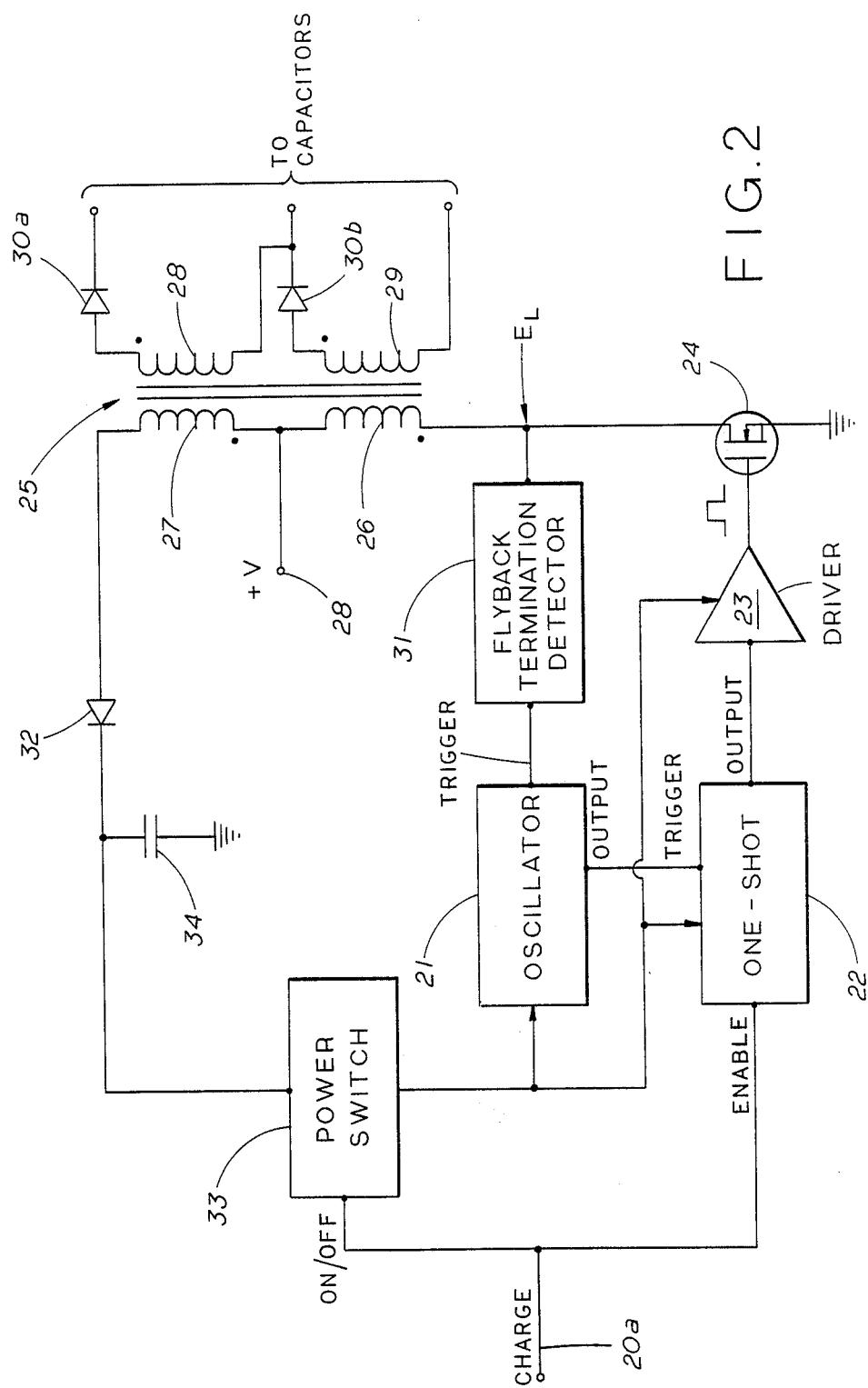
FIG. 2 is block diagram of the charging circuit block of FIG. 1.

As shown in FIG. 2, the charging circuit preferably has a free-running oscillator 21, the output terminal of which is connected to the trigger terminal of a one-shot 22. The output terminal of the one-shot 22 in turn connects to the input of a driver 23, the output of which controls the gate of an N-channel power FET 24. The source of the power FET 24 is connected to ground while the drain connects to one end of a first primary coil 26 which comprises part of a charging transformer 25. The first primary coil 26 connects at its opposite end to one end of a second primary coil 27. The opposite end of the second primary coil 27 connects to the anode of a diode 32, the cathode of which in turn connects to one terminal of a power switch 33. A capacitor 34 is also preferably connected between the cathode of the diode 32 and ground to inhibit power spikes. The other terminal of the power switch 33 connects to the positive supply input terminals of the oscillator, one shot, and driver 21, 22, and 23 respectively. A control line 20a labelled "charge," connects the controller 9 through the voltage level detector 19 to the enable terminal of the one-shot 22, and to the on/off terminal of the power switch 33.

The secondary of the charging transformer 25 contains first and second secondary coils 28,29. The first secondary coil 28 connects at one end to the anode of a first diode 30a. The cathode terminal of the first diode 30a in turn connects to terminal A of the first charge-storing capacitor 12. At its opposite end, the first secondary coil 28 connects to the common terminal B of the first and second series charge-storing capacitors 12,13. The second secondary coil 29 connects at one end to the anode of a second diode 30b, the cathode of which connects to the common terminal B of the first and second series charge-storing capacitors 12,13. At its opposite end, the second secondary coil 29 connects to terminal C of the second charge-storing capacitor 13.

Also connected to the drain of the power FET 24 is the input of a "flyback" or charge coupling cycle termination detector 31. The output of the "flyback" termination detector 31 is connected to the trigger terminal of the oscillator 21.

A positive voltage supply 28 is tapped between the first and second primary coils 26,27 of the charging transformer 25. The positive voltage supply 28 is preferably capable of providing nine (9) volts DC over a long period of time. In the presently preferred embodiment, three lithium cells stacked in series have been found suitable for this purpose.

Figure 3:
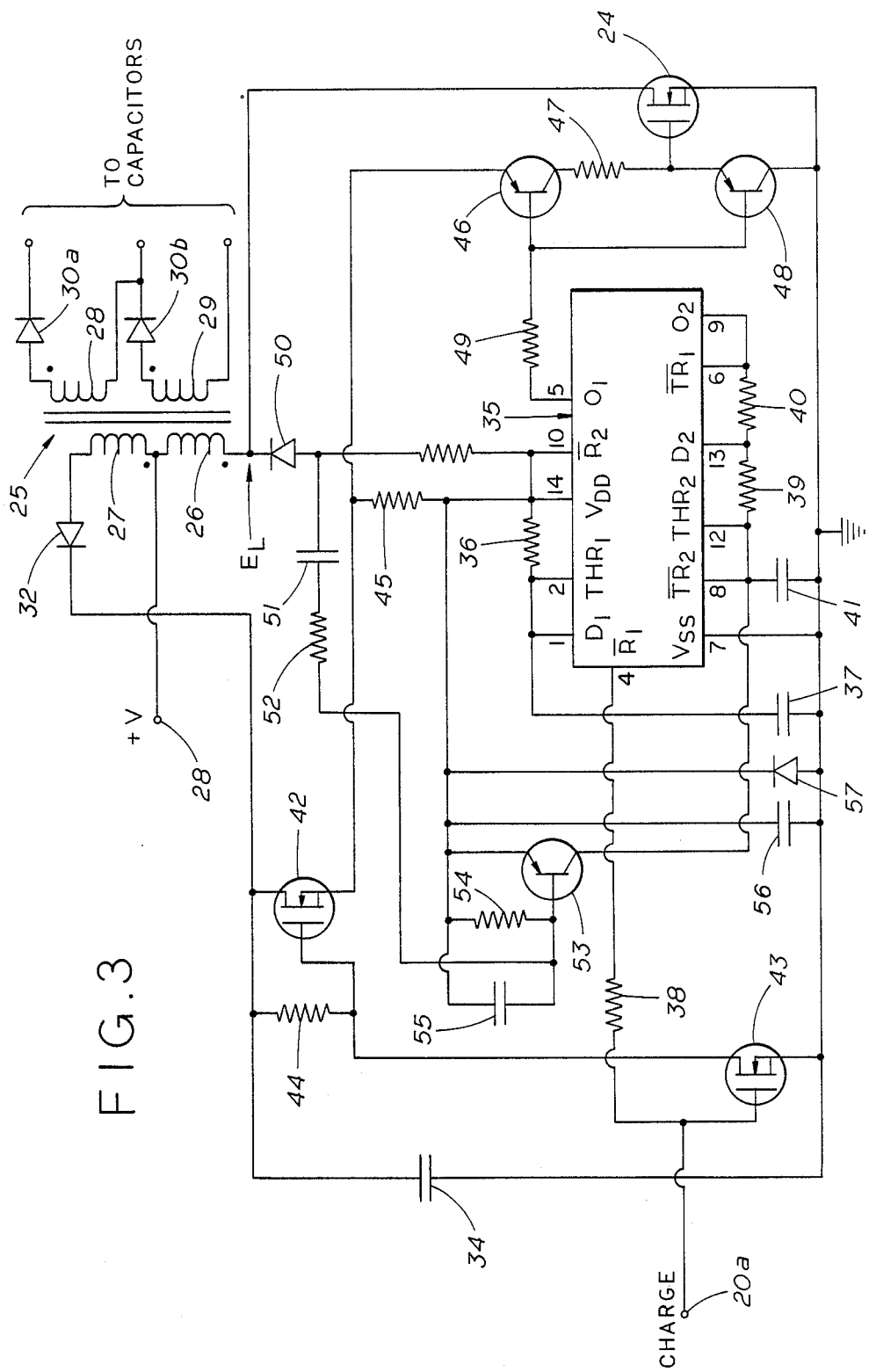
FIG. 3 is a schematic diagram of the charging circuit block diagram of FIG. 2.

As illustrated in the schematic diagram of FIG. 3, an Intersil ICM-7556 dual general purpose timer 35 or equivalent may be used to implement the oscillator 21 and oneshot 22. The ICM-7556 is a CMOS device and is preferred over bipolar equivalents for its very low operating current requirement as compared to equivalent bipolar devices. Additionally, the ICM-7556, being a dual device, provides both space and component savings.

In the presently preferred embodiment, pins 1–6 of the ICM-7556 are used to implement the one-shot 22. A resistor 36 is connected at one end to the supply voltage pin (pin 14) and at the other end to a capacitor 37, and to the one-shot discharge and threshold pins (pins 1,2) in parallel. The opposite end of the capacitor 37 is connected to ground. The RC time constant established by the resistor 36 and capacitor 37 controls the duration of the one-shot output pulse. It has been found that the best efficiency in charging the first and second series capacitors 12,13 is obtained when the duration of the output pulse is approximately eight (8) microseconds, which value is preferred for that reason. This value of duration is preferably obtained by choosing a value for the resistor 36 of approximately 80K ohms, and for the capacitor of approximately 100 picofarads. Although other combinations of resistance and capacitance would also provide the appropriate duration value, it is preferable to use high resistance and low capacitance values to minimize the current drain on the positive voltage source 28.

The one-shot 22 is enabled by the application of a positive signal to the one-shot reset pin (pin 4). Such a signal is supplied by the controller (not shown) through the voltage level detector 19 by way of the "charge" control line 20a. A series 10K ohm resistor 38 preferably limits the current flow to the one-shot reset pin (pin 4). A positive pulse having the selected duration is output on the one-shot output pin (pin 5) when the enabled one-shot 22 receives a negative-going trigger pulse on the one-shot trigger pin (pin 6). In the presently preferred embodiment described herein, the one-shot trigger pin (pin 6) is tied directly to the oscillator output pin (pin 9) and the oscillator 21 is used to trigger the one-shot 22.

Pins 8–13 of the ICM-7556 are used in the presently preferred embodiment to implement the oscillator 21. As is well known to those skilled in the art, the oscillator 21 can be implemented by simply having the ICM-7556 trigger itself. In this embodiment, a first resistor 40 is connected at one end to the oscillator output pin (pin 9) and at the other end to the oscillator discharge pin (pin 13). A second resistor 39 is connected at one end to the oscillator discharge pin (pin 13) and at the other end to the oscillator threshold pin (pin 12). The oscillator threshold pin (pin 12) is connected directly to the oscillator trigger pin (pin 8). A capacitor 41 is connected between the oscillator trigger pin (pin 8) and ground. As mentioned above, the oscillator output pin (pin 9) is connected directly to the one-shot trigger pin (pin 6). Preferably, the oscillator 21 is always enabled when supply voltage is present at the supply pin (pin 14). This is accomplished by connecting the oscillator reset pin (pin 10) directly to the supply voltage pin (pin 14). The frequency and duty cycle of the oscillator 21 output signal are controlled by the value of the resistors 39,40 and the capacitor 41. It has been found that the best efficiency in charging the first and second charge-storing capacitors 12,13 is obtained when the oscillator 21 output signal has a frequency of approximately 8.8 KHz, which accordingly comprises a preferred value of frequency. It has also been found that an oscillator output pulse having a duration of approximately one microsecond is sufficient to trigger the one-shot 22. These preferred frequency and duty cycle values are preferably obtained by using a resistor 40 having a value of approximately 800K ohms, a resistor 39 having a value of approximately 10K ohms, and a capacitor 41 having a value of approximately 100 picofarads. Of course, other combinations of resistance and capacitance values could also be used to obtain the preferred frequency and duty cycle values. However, as previously mentioned, it is preferable to use high resistance values and low capacitance values in order to minimize the current drain on the positive voltage source 28.

The one-shot output pin (pin 5) is connected to the input of the driver 23. The driver 23 preferably comprises an NPN transistor 46 which has its collector connected to the drain of the P-channel FET 42 comprising part of the power switch 33, and its emitter connected to the emitter of a PNP transistor 48 through a series 240 ohm resistor 47. The collector of the PNP transistor 48 is in turn connected to ground. The bases of the NPN and PNP transistors 46,48 are connected together. The one-shot 22 output pin (pin 5) is connected to the base of the NPN transistor 46 through a 1.2K ohm resistor 49. The NPN transistor 46 is suitably a 2N2222A type or equivalent, and the PNP transistor 48 is suitably a 2N2907A type or equivalent. The output of the driver 23 is taken off the emitter of the PNP transistor 48, which is connected to the gate of the power FET 24.

The power FET 24 itself is preferably an N-channel FET having very low impedance in the conductive state, and capable of withstanding high peak currents. The IRFC140 type FET, for example, has an impedance in the conductive state of approximately 0.085 ohms and is suitable for use.

The connection of the power FET 24 to the charging transformer 25, and the electrical interconnections of the transformer 25 have been previously described. The charging transformer 25 of the presently preferred embodiment has a Ferroxcube 1408 PA1603B7 pot core or equivalent. The first primary coil 26 preferably comprises seven turns of #26 magnet wire, and the second primary coil comprises 12 turns of #36 magnet wire. It has been found that by winding the first and second secondary coils 28,29 in a bifilar manner stray capacitance is reduced and charging efficiency is improved. Therefore, the first and second secondary coils 28,29 are preferably wound simultaneously using bifilar magnet wire such as the bifilar magnet wire No. B2404211 manufactured by MWS Wire Industries of Westlake Village, California. Each of the first and second secondary coils 28,29 preferably comprises 140 turns of #40 magnet wire. The first and second diodes 30a,30b in the secondary of the charging transformer 25 are both suitably IN4937 type or equivalent.

Under a typical operating load, the output of the positive voltage supply 28 is reduced to approximately 5.5 volts. However, the positive voltage source 28 is tapped into the primary of the charging transformer 25 between the first and second primary coils 26,27 to obtain a voltage doubler effect. Thus, the voltage at the anode of the diode 32 is approximately 2.7 times the voltage at the positive voltage supply 28 with respect to ground and, therefore, approximately 13.75 volts is supplied to the supply pin (pin 14) of the ICM-7556 under load.

The interconnection of the "flyback" termination detector 31, the power FET 24, and the oscillator 21 has been described above. The "flyback" termination detector 31 comprises a diode 50 having its cathode connected to the drain of the power FET 24, and its anode connected to the base of a PNP transistor 53 through a series 100 picofarad blocking capacitor 51 and 1.6K ohm resistor 52. The emitter of the PNP transistor 53 is connected to the supply voltage pin (pin 14), and the collector is connected to the oscillator trigger pin (pin 8). A 7.5K ohm resistor 54 and a 100 picofarad capacitor 55 are connected in parallel between the base and emitter of the PNP transistor 53. The PNP transistor is preferably a 2N2907A type or equivalent.

In addition to the previously described connections to the ICM-7556 35, it also is connected to ground at pin 7. Further, a 0.1 microfarad capacitor 56 and zener diode 57 are preferably connected in parallel between the supply and ground pins, 14 and 7, to limit maximum voltage and inhibit surges to the ICM-7556 35. The zener diode 57 is suitably an IN965A type or equivalent which limits the voltage across it to 15V +/−10%.

The operating voltage for the ICM-7556 35 is supplied through the power switch 33. The power switch 33 comprises a P-channel FET 42 having its source connected to the cathode of the diode 32 and its gate connected to the drain of an N-channel FET 43. A 100K ohm resistor 44 is connected between the gate and source of the P-channel FET 42. The drain of the P-channel FET 42 is connected to the supply voltage pin (pin 14) of the ICM-7556 35 through a 200 ohm resistor 45. The source of the N-channel FET 43 is connected to ground and its gate is connected to the "charge" control line 20a. The diode 32 is suitably an IN4973 or equivalent. The P-channel FET is suitably a VP01 type or equivalent, and the N-channel FET is suitably a VN2222K, VN10K or equivalent.

Operation of the charging circuit 10 will now be described with reference to FIGS. 3, 8a and 8b. As shown in FIG. 8a, when the controller senses that the heart 14 has entered a state of fibrillation, it generates a positive signal on the "charge" control line 20a. This positive signal causes the N-channel FET 43 to become conductive, thus pulling the gate of the P-channel FET to nearly ground potential. The potential at the source of the P-channel FET 42 comprising power switch 33 is much higher than ground, and the P-channel FET 42, therefore, becomes conductive. The 100K ohm resistor 44 between the source and gate of the P-channel FET 42 helps smooth its turn-on. With the power switch 33 activated, operating voltage is present on the supply pin (pin 14) of the ICM-7556 35. Activation of the power switch 33 not only supplies operating power to the one-shot 22 and oscillator 21, but also enables the oscillator 21 by applying a positive signal to the oscillator reset pin (pin 10). At the same time, the positive signal on the "charge" control line 20a enables the one-shot 22 by applying a positive signal to the one-shot reset pin (pin 4).

Referring to FIGS. 3, 8a, and 8b, initially the potential on the one-shot and oscillator trigger pins (pins 6,8) and threshold pins (pins 2,12) is low. Given this initial condition, the application of a positive signal to the one-shot and oscillator reset pins (pins 4,10) forces the one-shot and oscillator output pins (pins 5,9) high. With the one-shot output pin (pin 5) high, the internal discharge path through the one-shot discharge pin (pin 1) opens, and the capacitor 37 begins to charge through resistor 36 to the voltage level at the supply pin (pin 14). At the same time, the one-shot trigger pin (pin 6) is held high by the oscillator output pin (pin 5), which causes the capacitor 41 to charge through resistors 39,40. When the voltage at the one-shot threshold pin (pin 2) has risen to approximately $\frac{2}{3}$ of the voltage at the supply pin (pin 14) (approximately 8 microseconds), the one-shot output pin (pin 5) is driven low, the internal discharge path through the one-shot discharge pin (pin 1) is closed, and the capacitor 37 discharges. The one-shot output pin (pin 5) remains low until the one-shot trigger pin (pin 6) again goes low. The one-shot trigger pin (pin 6) does not go low until the oscillator output pin (pin 9) goes low. This occurs when the capacitor 41 has charged to $\frac{2}{3}$ of the voltage at the supply pin (pin 14) (approximately 113 microseconds). When the capacitor 41 has charged to $\frac{2}{3}$ of the voltage at pin 14, the oscillator output pin (pin 9) is driven low, the internal discharge path through the oscillator discharge pin (pin 13) is closed, and the capacitor 41 discharges. With the oscillator output pin (pin 9) driven low, the one-shot trigger pin (pin 6) also goes low. This in turn causes the one-shot output pin (pin 5) to again go high. The oscillator output pin (pin 9) remains low until the capacitor 41 has discharged to $\frac{1}{3}$ of the voltage at the supply pin (pin 14) (approximately 1 microsecond), at which time it again goes high, pulling the one-shot trigger pin (pin 6) high. This sequence of events continues with the oscillator output pin (pin 9) going low approximately every 113 microseconds to trigger the one-shot trigger pin (pin 6) to cause the one-shot 22 to generate a pulse of approximately 8 microseconds duration at the one-shot output pin (pin 5), except, as will be described below, when the "flyback" termination detector 31 intervenes.

The primary function of the driver 23 is to very quickly turn the power FET 24 on and off. This is necessitated by the rather large gate to source capacitance inherent in power FET devices which slows their response time. When the one-shot output pin (pin 5) goes high, the base-emitter junction of the NPN transistor 46 immediately becomes forward biased and the NPN transistor 46 conducts. At the same time, the PNP transistor 48 becomes non-conductive. As a result, the gate of the power FET 24 is rapidly pulled high, turning it on and making it conductive. The turn-on time of the power FET 24 is preferably limited slightly by including the series resistor 47 having a low resistance value of 240 ohms to avoid introducing any current spikes into the supply pin (pin 14) of the ICM-7556 35. When the one-shot output pin (pin 5) goes low again after approximately eight (8) microseconds, the emitter-base junction of the PNP transistor 48 immediately becomes forward biased and the PNP transistor 48 becomes conductive. At the same time, the NPN transistor 46 becomes non-conductive. As a result, the gate of the power FET 24 is immediately pulled to ground potential, making it non-conductive and quickly turning it off. Since the gate capacitance of the power FET is shunted directly to ground, no effects are seen at pin 14 of the ICM-7556 when the power FET 24 is turned off quickly.

Referring to FIGS. 3 and 8b, when the one-shot output pin (pin 5) is high, and the power FET 24 is conducting, current flows through the first primary coil 26 and through the power FET 24 to ground, thus generating charge in the primary coil 26. This current flow tries to force a reverse flow in the first and second secondary coils 28,29 of the transformer 25. However, the reverse biased diodes 30a,30b prevent the flow of reverse current during the charge generation cycle. When the one-shot output pin (pin 5) goes low after approximately eight (8) microseconds, and the power FET 24 ceases to conduct, the charging circuit enters what has been referred to as the "flyback" cycle or charge coupling cycle. During the "flyback" cycle, the inductive inertia of transformer 25 tries to force the current stored in the primary to flow in the same direction as when the power FET 24 was conducting. Since the power FET 24 is no longer conductive, however, a large voltage $E_L$ in excess of the positive voltage supply 28 is generated at its drain. At the same time, the magnetic field coupling the transformer 25 primary and secondary circuits results in a positive voltage being simultaneously of the secondary coils 28,29 so that the first and second diodes 30a,30b become conductive. When the diodes 30a,30b are conductive, current flows in each of the secondary coils 28,29 to simultaneously charge the first and second charge-storing capacitors 12,13 respectively. The "flyback" cycle ends when the excess voltage $E_L$ at the drain of the power FET 24 has dissipated to the level of the positive voltage supply 28. At this point, no current flows through coils 28 and 29 and the magnetic field coupling the transformer 25 primary and secondary circuits collapses. Also at this point, the first and second charge-storing capacitors 12,13 have been charged with substantially all of the inductive energy developed during the charge generation cycle.

It is a well known principle of electricity that it takes a greater amount of time for an uncharged capacitor to store a unit of inductive energy than for a partially charged capacitor to store an additional unit of inductive energy. A corollary of this principle is that generally the greater the existing charge on a capacitor, the less time required for it to store an additional unit of energy. Thus, as illustrated in FIG. 8b, during the "flyback" or charge coupling cycle the first and second charge-storing capacitors remove the energy stored in secondary coils 28,29 at a rate proportional to the voltage on the charge-storing capacitors 12,13. The energy removal is slowest, and the charging time the greatest when the charge-storing capacitors 12,13 are completely uncharged. Both gradually decrease with each "flyback" cycle as the charge-storing capacitors 12,13 become more fully charged. It should be apparent therefore, that the duration of each succeeding "flyback" cycle decreases correspondingly. Accordingly, it is preferable to set the frequency of the oscillator 21 so that the oscillator period is longer than the time required for the first and second series capacitors 12,13 to store all of the generated inductive energy during the first, and hence longest, "flyback" cycle. If the oscillator 21 period is shorter than the duration of a "flyback" cycle, the oscillator 21 will trigger the one-shot 22, causing the power FET 24 to become conductive, before the "flyback" cycle is completed. This in turn causes the portion of the generated inductive energy not yet stored by the first and second charge-storing capacitors 12,13 to be shunted to ground. This is highly undesirable since it wastes energy generated by the depletable voltage source 28. It may also make additional charging cycles necessary and delay the delivery of defibrillation pulses to the heart 14. It should be apparent, however, that by setting the oscillator 21 period long enough to accommodate the longest expected "flyback" cycle, additional time is used to charge the first and second charge-storing capacitors 12,13 due to the fact that the duration of each "flyback" cycle decreases.

For this reason, the presently preferred embodiment includes a "flyback" termination detector 31. The "flyback" termination detector 31 minimizes the time and energy necessary to fully charge the first and second charge-storing capacitors 12,13 by sensing the voltage $E_L$ at the drain of the power FET 24 to determine exactly when the "flyback" cycle has completed, and then triggering the one-shot 22 by driving the oscillator output pin (pin 9) low.

Initially, when the controller places a positive signal on the "charge" control line 20a, the one-shot output pin (pin 5) goes high and the power FET 24 becomes conductive causing the emitter-base junction of the PNP transistor 53 to become forward biased and the transistor to conduct. During the time the PNP transistor 53 is conductive, it pulls the oscillator trigger and threshold pins (pins 8,12) high to the level of the supply pin (pin 14). This in turn drives the oscillator output and one-shot trigger pins (pins 6,9) low and would cause the one-shot output pin (pin 5) to go high if it were not already high. The PNP transistor 53 only remains conductive for about one microsecond, the length of time it takes for the blocking capacitor 51 to charge through the resistors 52,54 to approximately the level of the supply pin (pin 14). When the blocking capacitor 51 charges to this level, the emitter-base junction of the PNP transistor 53 is no longer forward biased and the transistor becomes non-conductive, releasing the oscillator trigger and threshold pins (pins 8,12).

Thereafter, each time the one-shot output pin (pin 5) goes low and the "flyback" cycle begins, the voltage $E_L$ at the drain of the power FET 24 becomes much greater than the voltage at the supply pin (pin 14). During this part of the "flyback" cycle, the diode 50 is reverse biased. This maintains the base potential of the PNP transistor 53 at a level sufficient to reverse bias the emitter-base junction and keep the PNP transistor 53 non-conductive. When the voltage $E_L$ at the drain of the power FET 24 dissipates to the level of the supply pin (pin 14), however, indicating that the "flyback" cycle is completed, the diode 51 becomes forward biased, causing current to flow out of the base of the PNP transistor 53, and forward biasing the emitter-base junction. The PNP transistor 53 then conducts and pulls the oscillator threshold and trigger pins (pins 8,12) high, causing the oscillator output and one-shot trigger pins (pins 6,9) to go low, and triggering the one-shot 22 to start a new charge generation cycle.

Charging of the charge-storing capacitors 12,13 continues cyclically in the above-described manner for as long as the signal on the "charge" control line 20a remains positive. When the "charge" control line 20a goes low, one-shot 22 is inhibited, the power switch 33 is de-activated, and the N-channel FET 43 ceases to conduct. This in turn causes the P-channel FET 42 to also become non-conductive, and removes the supply voltage from the supply pin (pin 14) of the ICM-7556 35, thus disabling the one-shot 22 and oscillator 21 and minimizing the charging circuit standby current.

Figure 4:
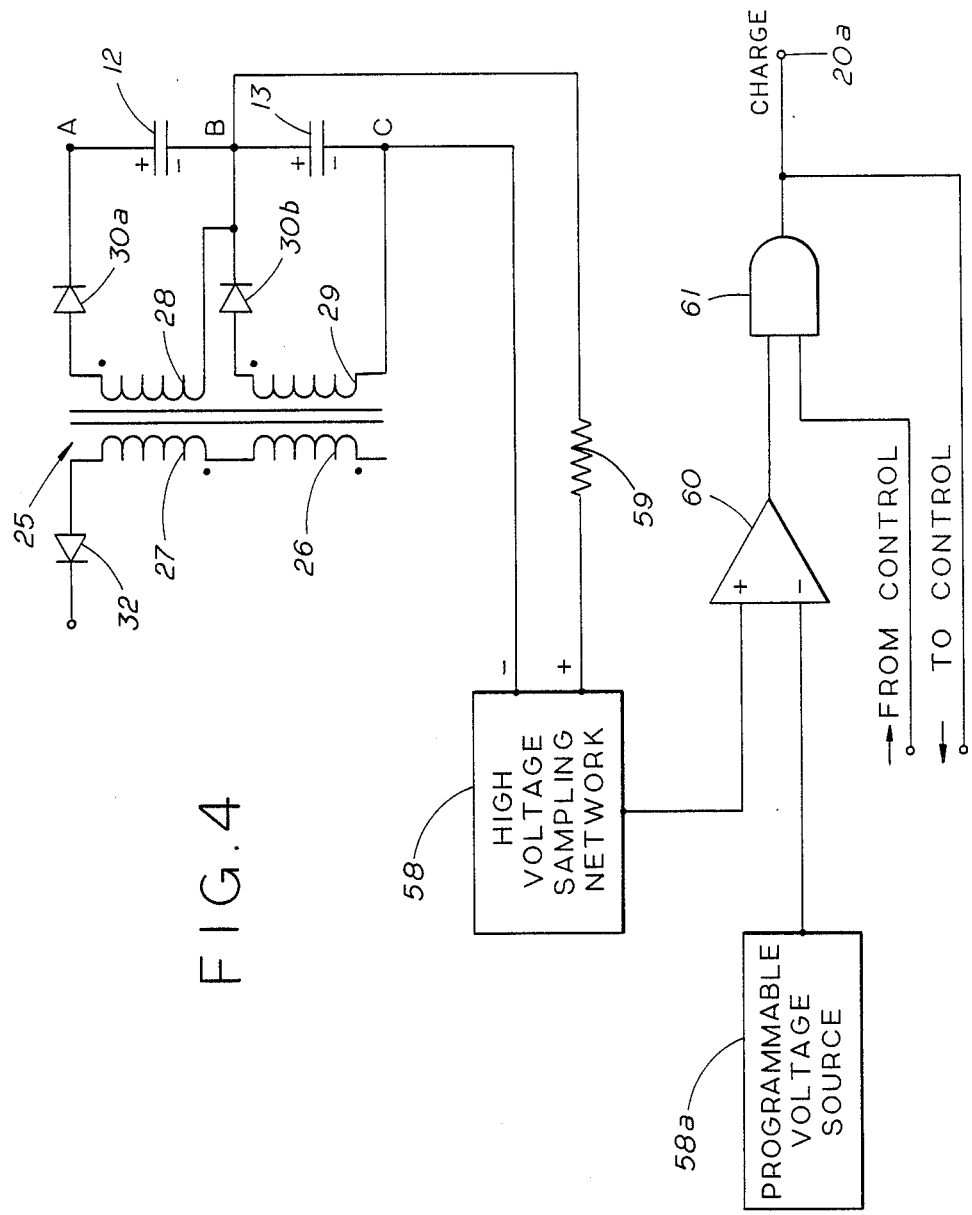
FIG. 4 is a block diagram of the voltage level regulation block component of FIG. 1.

As shown in FIGS. 1 and 4, a voltage level detector 19 preferably determines when the first and second charge-storing capacitors 12,13 are fully charged to a selected level, and pulls the "charge" control line 20a low to identify this condition to the controller and to disable the charging circuit 10. The voltage level detector 19 preferably comprises a high-impedance sampling network 58 electrically connected across the second charge-storing capacitor 13. A series 100K ohm resistor 59 is preferably placed in the lead from the common terminal B of the second charge-storing capacitor 13 to limit current flow. The output of the high-impedance sampling network 58 is connected to the positive terminal of a comparator 60. The negative terminal of the comparator 60 is connected to the output of a programmable voltage source 58a. The output of the comparator 60 is connected to one terminal of a two input AND gate 61. The other terminal of the AND gate 61 is connected to a line from the controller (not shown). The output of the AND gate 61 preferably comprises the "charge" control line 20a. The voltage level detector 19 can be incorporated as part of the charging circuit 10 itself or as a separate component. It is illustrated in FIG. 1 as a separate component. The high-impedance sampling network 58 is suitably implemented as a high-impedance scaling network of the type familiar to those skilled in the art. The programmable voltage source 58a is preferably a D-A converter or a similar programmable device, the operation of which can be controlled by a digital or analog controller. A conventional operational amplifier is suitable for use as the comparator 60.

In operation, the controller 9 programs the D-A converter or other programmable voltage source to produce an analog reference voltage corresponding to one half the desired total voltage of both series charge storing capacitors 12,13 when fully charged, assuming they are to be charged to equal levels as in the presently preferred embodiment. It should be apparent that the programmed reference voltage is not actually equal to one half the desired voltage but is scaled the same as the actual capacitor voltage sampled by the high-impedance sampling network 58. The high-impedance sampling network 58 produces a scaled analog voltage representative of the actual voltage across the second charge-storing capacitor 13. The comparator 60 generates a high output so long as the programmed reference voltage exceeds the measured, scaled voltage. This in turn causes the output of the AND gate 61, i.e., the "charge" line 20a, to remain high as long as the control signal from the controller (not shown) also remains high. When the "charge" line 20a is high, the charging circuit 10 is enabled and charges the first and second charge-storing capacitors 12,13. When the scaled analog voltage on the high-voltage sampling network 58 equals or exceeds the programmed reference voltage, the comparator 60 output goes low, driving the AND gate 61 output low, and disabling the charging circuit 10 from further charging the first and second charge-storing capacitors 12, 13.

Figure 5:
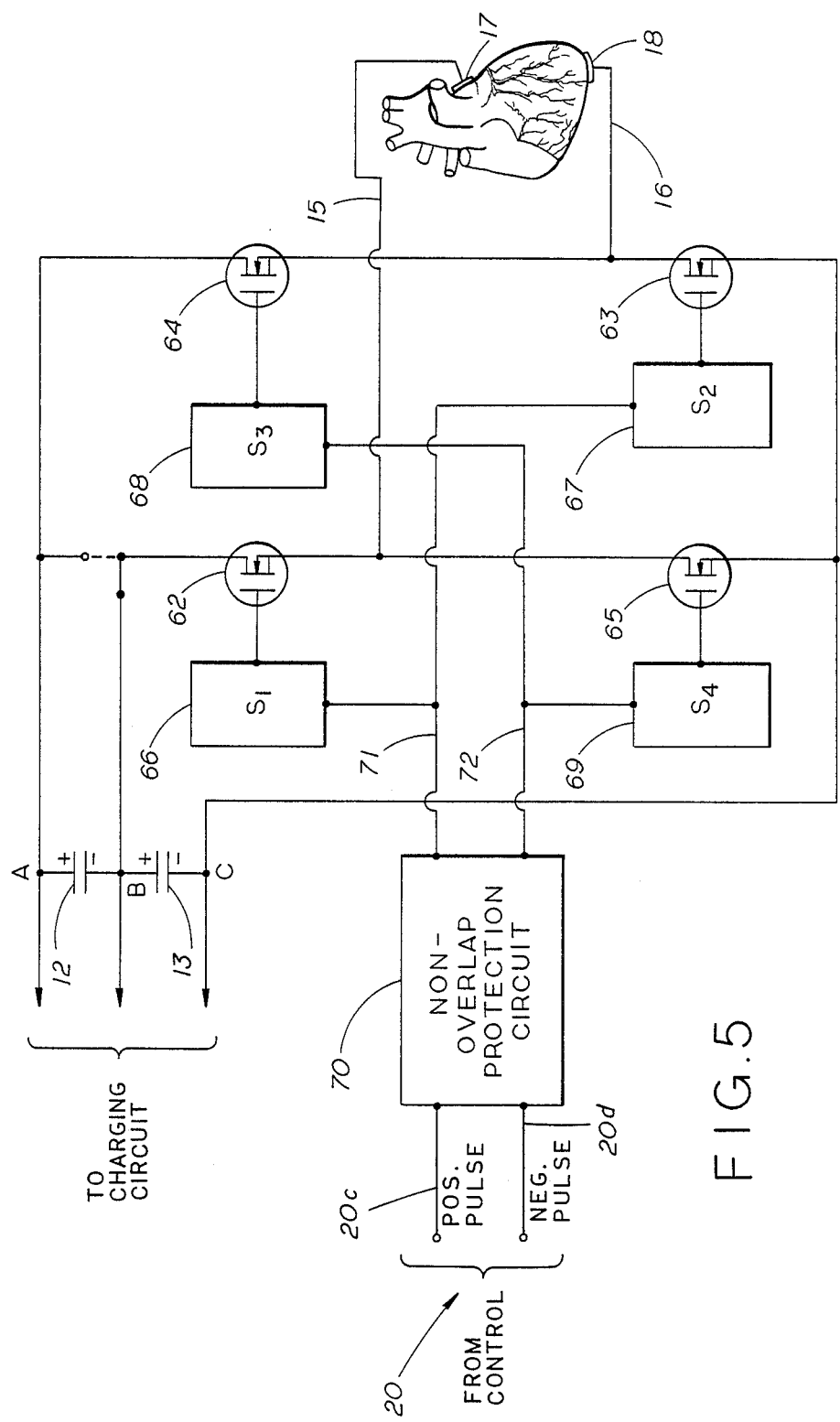
FIG. 5 is a block diagram of the multiphasic pulse generator block of FIG. 1 shown with a heart.

Referring to FIG. 5, the multiphasic pulse generator 11 uses the charge stored in the first and second charge-storing capacitors 12, 13 to generate a multiphasic defibrillation pulse waveform. The multiphasic pulse generator 11 preferably comprises first, second, third, and fourth power FETs 62, 63, 64, 65, and corresponding first, second, third, and fourth FET drivers (S1, S2, S3, S4) 66, 67, 68, 69. Preferably, the multiphasic pulse generator 11 also includes a non-overlap protection circuit 70. Each of the power FETs 62-65 is suitably an N-channel GEMFET such as the MGM20N50 manufactured by Motorola. GEMFETs are preferred for their ability to withstand the high peak and constant current encountered in heart defibrillation applications. The FET drivers 66-69 control the on/off conduction states of their respective power FETs 62-65 by controlling the gate potentials thereof. The FET drivers 62-65 themselves are preferably controlled by control signals from the controller in a manner to be described below.

As shown in FIG. 5, in the presently preferred embodiment, the FET drivers 66-69 are arranged in pairs, the first and second FET drivers 66,67 being one pair, and the third and fourth FET drivers 68,69 being a second pair. The first pair of drivers 66,67 control the on/off conduction states of the first and second power FETs 62,63 and the second pair of drivers 68, 69 control the on/off conduction states of the third and fourth power FETs 64,65. However, the FET drivers 66-69 can also be implemented and controlled individually to provide individual control of the power FETs 62-65 if desired. Such an arrangement provides additional flexibility at the expense of reduced size and power consumption.

In the preferred paired arrangement, it is critical that only one pair of power FETs be "on" or conducting at any particular time to prevent directly short circuiting the first and second charge-storing capacitors 12, 13. As will become apparent below, the non-overlap protection circuit 70 provides an extra safe-guard for the patient by preventing the occurrence of this condition.

As shown in FIG. 5, the drain of the first power FET 62 may be connected to either terminal A of the first charge-storing capacitor 12 or to the common terminal B. This selectable connection may be made by the manual placement of a jumper. However, it is preferable to use a double pole, single throw switch arrangement, preferably of the solid-state variety, and preferably controllable by control signals from the controller, to provide additional-flexibility for automatic operation. The source of the first power FET 62 comprises a first output terminal and is connected to one end of the conventional electrically conductive output lead 15, the other end of which is connected to the heart 14 via conductive patch 17. The gate of the first power FET 62 is connected to the output of the first FET driver 66. The drain of the second power FET 63 comprises a second output terminal and is connected to one end of the conventional electrically conductive return lead 16, the other end of which has a conductive patch 18 which is connected to the heart 14. The source of the second power FET 63 is connected to terminal C of the second charge-storing capacitor 13, and its gate is connected to the output of the second FET driver 67. The drain of the third power FET 64 is connected to terminal A of the first charge-storing capacitor 12, and its source is connected to the heart 14 by the conventional electrically conductive lead 16 and conductive patch 18. Its gate is connected to the output of the third FET driver 68. The drain of the fourth power FET 65 is connected to the heart 14 by the conventional conductive lead 15 and conductive patch 17. Its source is connected to terminal C of the second charge-storing capacitor 13, and its base is connected to the output of the fourth FET driver 69.

The non-overlap protection circuit 70 is connected to the controller (not shown) by a "pos pulse" and a "neg pulse" control line 20b,20c. In the preferred paired arrangement, the non-overlap protection circuit 70 connects to the first and second FET drivers 66,67 via a first lead 71 and to the third and fourth FET drivers 68,69 via a second lead 72. In a nonpaired arrangement, separate leads would connect the non-overlap protection circuit 70 with each FET driver 66–69. It is also possible to eliminate the nonoverlap protection circuit 70 entirely and have the controller control the FET drivers 66–69 directly. However, such an arrangement is less preferable because of the increased risk of controller malfunction causing direct short-circuiting of he capacitors 12,13.

Figures 6, 7:
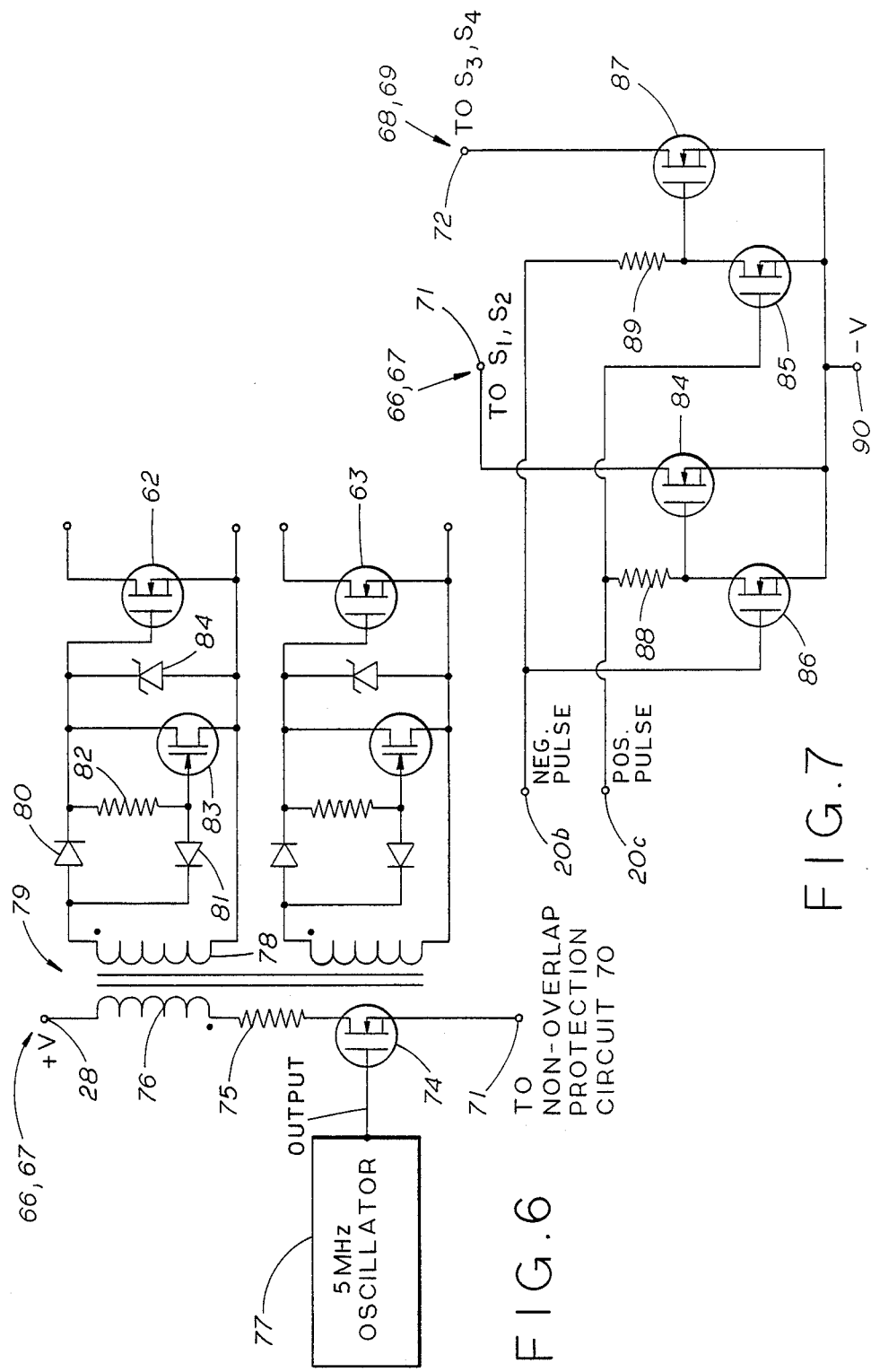
FIG. 6 is a schematic diagram of the FET driver circuits S1-S4 shown in FIG. 5.
FIG. 7 is a schematic diagram of the nonoverlap protection circuit shown in FIG. 5.

In the preferred paired arrangement shown in FIG. 6, FET drivers 66,67 are illustrated as a single oscillator-driven isolation transformer circuit 79 in which they comprise separate but identical secondary sub-circuits. The FET drivers 68,69 are implemented in a second identical circuit. It is preferable to implement the FET drivers 66–69 in this way both to minimize the on/off speed of the power FETs 62–65, which inherently possess rather large gate to source capacitance, and to provide isolation of the power FETs 62–65. In view of the fact that each of the FET drivers 66–69 in the presently preferred embodiment is identical in structure and operation, the following description, although limited in terms to FET driver 66 and power FET 62, will be understood to apply equally to FET drivers 67–69 and power FETs 63–65 as well. It is also understood that in the preferred paired arrangement, FET driver pair 66,67 controls FETs 62 and 63 simultaneously, and FET driver pair 68,69 controls FETs 64 and 65 simultaneously.

The oscillator 77 is preferably a conventional CMOS type oscillator capable of running at 5 MHz. A two inverter RC CMOS oscillator, for example, has been found suitable for use in the presently preferred embodiment. The output of the oscillator 77 is connected to the gate of an N-channel FET 74 in the primary of the isolation transformer 79. The drain of the N-channel FET 74 is in turn connected to the positive voltage supply 28 through a series 100 ohm resistor 75 and a primary coil 76 preferably comprising 10 turns of #40 magnet wire. The source of the N-channel FET 74 is connected to the non-overlap protection circuit 70 by lead 71 and from there to a negative voltage supply 90, assuming that the non-overlap protection circuit 70 has enabled the FET drivers 66,67 as will be described in detail below. A secondary coil 78 of the isolation transformer 79, preferably comprising 40 turns of #40 magnet wire, has one end connected to the anode of a first diode 80 and to the cathode of a second diode 81. At the opposite end, it connects to the source of the power FET 62. The cathode of the first diode 80 connects to the drain of an N-channel JFET 83, and to the gate of the JFET 83 through a 1 M ohm resistor 82. A JFET is preferred for this application because it is a depletion mode device and exhibits a low drain to source impedance in the absence of gate drive, which is critical for assuring the power FETs are normally non-conducting. The gate of the JFET 83 is also connected to the anode of the second diode 81, the cathode of which connects to the anode of the first diode 80. The drain of the JFET 83 is connected to the gate of the first power FET 62 and its source is connected to the source of the first power FET 62. A zener diode 84 has its cathode connected to the gate of the first power FET 62 and its anode connected to the source of the first power FET 62.

The non-overlap protection circuit 70 performs the function of enabling and disabling the FET drivers 66–69 in response to control signals from the controller. As shown in FIG. 7, the non-overlap protection circuit 70 includes a first, second, third, and fourth N-channel FET 84–87. The drain of the first FET 84 connects to the source of the N-channel FET 74 in the primary of the isolation transformer 79. The gate of the first FET 84 connects to the "pos pulse" line 20c through a 200K ohm resistor 88, and its source connects to the negative voltage supply 90. The drain of the second FET 85 connects in parallel to the gate of the fourth FET 87, and through a 200K ohm resistor 89 to the "neg pulse" control line 20b. The gate of the second FET 85 connects directly to the "pos pulse" control line 20c, and its source connects to the negative voltage supply 90. The drain of the third FET 86 connects in parallel to the gate of the first FET 84 and through the 200K ohm resistor 88 to the "pos pulse" control line 20c. The gate of the third FET 86 connects directly to the "neg pulse" control line 20b, and its source connects to the negative voltage supply 90. The drain of the fourth FET 87 connects to the source of the N-channel FET 74 in the primary of the isolation transformer 79 comprising part of the third and fourth FET drivers 68,69 (S3,S4). The gate of the fourth FET 87 connects to the "neg pulse" control line 20b through the 200K ohm resistor 89, and its source connects to the negative voltage supply 90.

The negative voltage supply 90 is preferably a −9 volt DC supply derived in any conventional manner from the positive voltage supply 28. Each of the FETs 84–87 is suitably a VN10K FET or equivalent.

The operation of the multiphasic pulse generator 11 will now be described with respect to an exemplary multiphasic waveform illustrated in FIG. 8c. The illustrated waveform is thought to be a particularly effective form for arresting ventricular fibrillation. After the voltage level detector 19 has identified to the controller that the charge-storing capacitors 12,13 are completely charged, as described above, the controller initiates the generation of a multiphasic defibrillation pulse waveform having the selected parameters by alternately pulling the "pos pulse" and "neg pulse" control lines 20b, 20c high, and also by controlling the connection of the drain of the first power FET 62 to terminals A and B. In particular, to generate the multiphasic defibrillation pulse waveform shown in FIG. 8c, with the drain of the first power FET 62 connected to terminal B, the controller first pulls the "pos pulse" control line 20c high to generate an initial set-up pulse 100. When the "pos pulse" control line 20c goes high, the gate of the first FET 84 in the non-overlap protection circuit 70 is pulled high causing the first FET 84 to conduct. This establishes a current path through the primary of the isolation transformer 79 of the first and second FET drivers 66,67 thus enabling them to turn the first and second power FETs 62,63 to the "on" conduction state. At the same time, the gate of the second FET 85 is also pulled high, causing it to conduct, which in turn causes the gate of the fourth FET 87 to be pulled low, causing it to be non-conductive, breaking the current path through the primary of the isolation transformer of the third and fourth FET drivers 68,69 and disabling them from turning the third and fourth power FETs 64,65 to the "on" conduction state.

With the first and second FET drivers 66,67 enabled, the output of the 5 MHz oscillator 77 on the gate of the N-channel FET 74 generates an alternating current flow in the primary coil 76 which is magnetically coupled to the secondary coil 78. The first diode 80 rectifies the positive half cycle of the alternating signal and conducts it to the drain of the JFET 83 and the gate of the first power FET 6. The second diode 81 rectifies the negative half cycle of the alternating signal and couples it to the gate of the JFET 83. Due to the gate capacitance inherent in FET devices, neither the JFET 83 nor the first power FET 62 responds to the zero half cycles of the respective rectified signals at their respective gates. Instead, each device reacts as though a steady state DC voltage had been applied. Thus, the gate of the first power FET 62 is quickly pulled high turning it to the "on" conduction state. The same thing happens simultaneously to the second power FET 63. At the same time, the gate of the JFET 83 is pulled low with resect to its source. This pinches off its conduction channel rendering it non-conductive.

With the first and second power FETs 62,63 in a conductive state, and the third and fourth power FETs 64,65 in a non-conductive state, a circuit is established from terminal B through the first power FET 62, the heart 14, and the second power FET 63 to terminal C. As shown in FIG. 8c, if the first and second series capacitors are initially charged to 400 V each, the voltage at the conductive patch 17 quickly rises to approximately 400 volts. It has been found in practice that it takes approximately 50 microseconds after the first and second power FETs 62,63 become conductive for the potential at the conductive patch 17 to reach 400 volts. It should be apparent that if the drain of the first power FET 62 is connected to terminal A, then an additive effect of the potentials of the charge storing capacitors is obtained and the initial positive set-up pulse 100 would have a peak of BOO volts. The first and second power FETs 62,63 remain conductive and the initial positive set-up pulse 100 is applied to the heart 14 for as long as the controller holds the "pos pulse" control line 20c high. Generally, it is preferable for the controller to hold the "pos pulse" control line 20c high for 5-8 milliseconds. During this time, the capacitors will discharge slightly through the heart 14 as illustrated.

When the "pos pulse" control line 20c goes low, the high signal on the gate of the first FET 84 in the non-overlap protection circuit 70 is removed and it becomes non-conductive, thus opening the current path in the isolation transformer 79 primary and disabling the generation of the oscillating signal therein. At the same time, the second FET 85 also becomes nonconductive and releases the gate of the fourth FET 87.

When the oscillating signal is removed from the primary of the isolation transformer 79 of the first and second FET drivers 66,67, the voltage at the gate of the JFET 83 quickly drops to zero. This releases the pinch-off condition on its conduction channel, and it becomes conductive, quickly pulling down the gate of the first power FET 62 and turning it to the "off" conduction state. The same thing happens simultaneously to the second FET driver 63 and power FET 67. As shown in FIG. 8c, when the first and second power FETs 62,63 cease to conduct, the voltage at the conductive patch 17 drops rapidly to zero. It has been found that due to the capacitive effects of the various FET devices and the isolation transformer 79, it takes approximately 10 microseconds for the voltage to drop to zero.

Figure 8C:
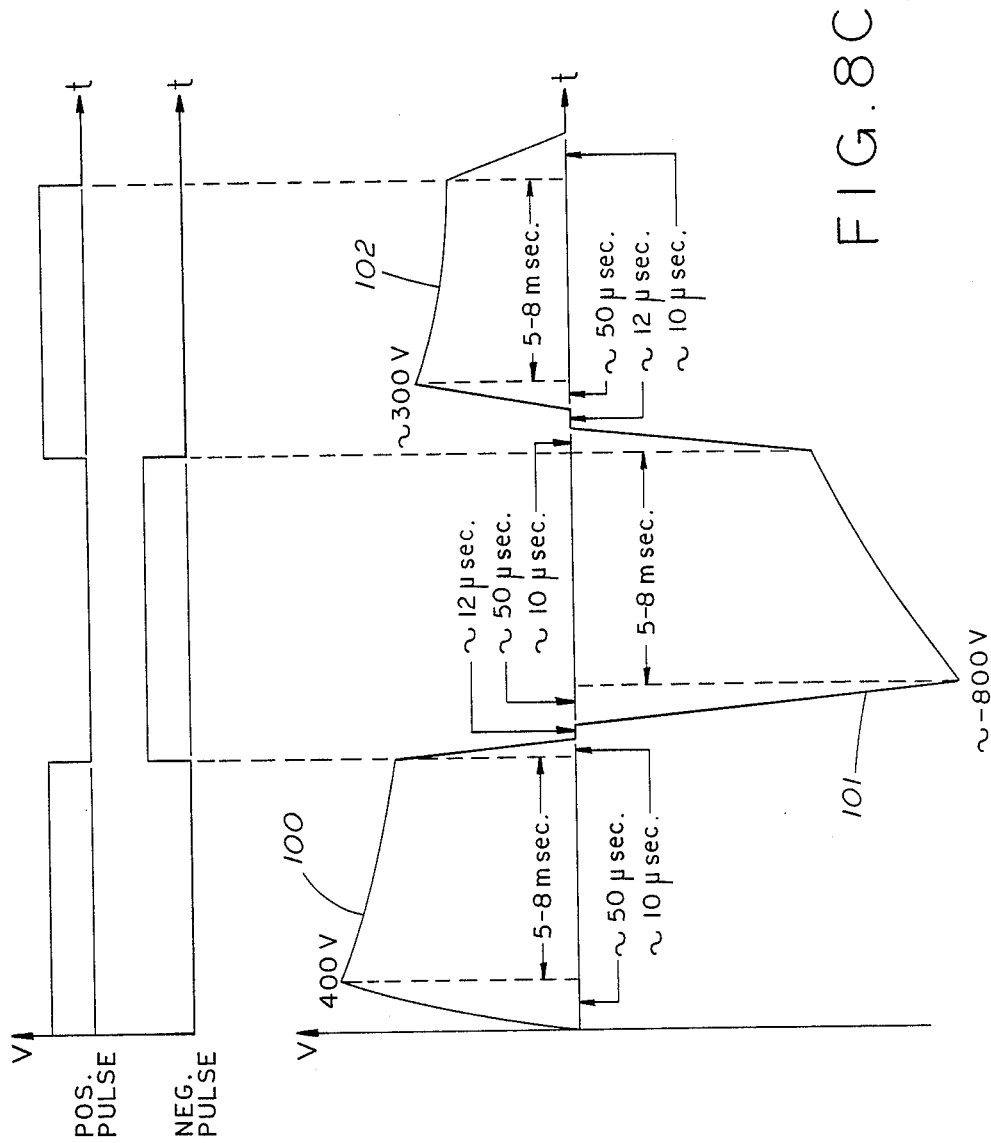
FIG. 8c is a diagram illustrating a typical multiphasic defibrillation pulse waveform for delivery to a heart.

To generate the primary cardioverting pulse 101 of the exemplary multiphasic waveform illustrated in FIG. 8c, the controller pulls the "neg pulse" control line 20b high. In the exemplary waveform of FIG. 8c, the "neg pulse" control line 20b is pulled high at the same time the "pos pulse" control line 20c is pulled low. It should be apparent by now that this will cause the converse of the previously described events to occur, i.e., the non-overlap protection circuit 70 will disable the first and second FET drivers 66,67 rendering the first and second power FETs 62,63 non-conductive. At the same time, the non-overlap protection circuit will enable the third and fourth FET drivers 68,69 which will turn the third and fourth power FETs 64,65 to the "on" conduction state. This in turn will establish a circuit from terminal A in the opposite direction through the third power FET 64, lead 16 and conductive patch 18, the heart 14, and the fourth power FET 65, to terminal C. When the third and fourth power FETs 64,65 become conductive, the voltage at the conductive patch rapidly rises within approximately 50 microseconds to approximately −800 volts, assuming again that each of the first and second charge-storing capacitors 12,13 is initially charged to approximately 400 volts. In effect, the potentials of the first and second charge-storing capacitors 12 and 13 are added with opposite polarity, or in other words are combined with a subtractive effect relative to ground potential, to obtain the −800 V pulse. When the controller pulls the "neg pulse" control line 20b low 5-8 milliseconds later, the non-overlap protection circuit 70 disables the third and fourth FET drivers 68,69 resulting in the third and fourth power FETs 64,65 being turned to the "off" conduction state. As a result, the voltage at the conductive patch 17 drops to approximately zero in approximately 10 microseconds. The trailing opposite polarity 102 of the exemplary multiphasic pulse waveform illustrated in FIG. 8c, is then generated in the same manner as previously described.

It should be apparent from the foregoing discussion that if for some reason both the "pos pulse" and "neg pulse" control lines 20 are simultaneously pulled high, the non-overlap protection circuit 70 will disable all FET drivers 66–69. It has also been found that the approximately 60 picofarad capacitance inherent in the FET devices used in the non-overlap protection circuit 70 in combination with the 200K ohm resistors 88,89 delay the on and off times of the first and fourth N-channel FETs 84,87 respectively. This delay, which amounts to approximately 12 microseconds, provides additional assurance that the first and second power FETs 62,63 and the third and fourth power FETs 64,65 will not be conductive at the same time in the preferred paired arrangement. This delay accounts for the small time gap between the sequential positive and negative pulses in the exemplary multiphasic pulse waveform of FIG. 8c.

It should be apparent from the foregoing description of an exemplary preferred embodiment that the present invention provides a great deal of flexibility in the generation of multiphasic cardioverting pulses. Indeed, flexibility is one of the great advantages of the present invention. For example, the sequence of pulling the "pos pulse" and "neg pulse" lines high and low can be varied to obtain additional multiphasic or other waveforms, including known unipolar pulses. In addition, the duration of each generated pulse can be accurately controlled. Further, if desired, the slope of the pulses applied to the heart can be adjusted by placing a resistance in the circuit paths between terminals A, B, and C and through the heart 14. Both full-height and half-height positive pulses can be generated by selectively connecting the drain of the first power FET 62 to terminal A or B to obtain or not obtain an additive effect of the potentials of the storage capacitors. In addition, half-height negative pulses can be generated in embodiments wherein the FET drivers 66-69 are individually controlled, by connecting the drain of the first power FET 62 to terminal B and controlling FET drivers 66 and 68 to make the first and third power FETs 62,64 conductive to obtain a subtractive effect relative to ground potential.

It will also be recognized by those skilled in the art that the present invention provides improved operational stability by providing bias for the FET drivers 66-69 from a source independent of the charge to be switched into circuit with the heart. It should also be apparent that the foregoing operation of the charging circuit 10, voltage level detector 19, and biphasic pulse generator 11 is fully automatic and requires no human intervention.

Additionally, it should be apparent that the invention is not limited to the specific number or arrangement of terminal potentials, power switches, and drivers described, but encompasses other possible arrangements as well. Also, those skilled in the art will recognize that the invention, although described in terms of a cardioverting application, will find use also in other implantable body stimulation applications.

Accordingly, it is understood that the presently preferred apparatus described herein in detail is merely illustrative of various aspects of the present invention and is not intended to be limiting. Various changes to the preferred embodiments described herein will be apparent to those skilled in the art. Such changes and modifications can be made without departing from the spirit and scope of the present invention. It is, therefore, intended that such changes and modifications be covered by the following claims and their equivalents.

I claim:

1. An apparatus for generating multiphasic defibrillation pulse waveforms by selectively switching the continuous output of a single multilevel source, comprising:
    first and second output terminal means for electrical connection to the heart;
    a plurality of charge storage means forming a single multilevel source, each said storage means storing an electrical charge to provide an output potential;
    low voltage power source means;
    charging means connected to said plurality of charge storage means and said low voltage power source means for charging each of said charge storage means to a level suitable to cause defibrillation of the heart;
    a plurality of switch means, each having control means operative to render the switch means conductive in response to a control signal, one switch means of said plurality being connected in circuit between a respective one of each said charge storage means and each of said first and second output terminal means for connecting the potential provided by the said charge storage means to the respective terminal means when said switch means is conductive sand disconnecting the potential provided by said charge storage means form the respective terminal means when said switch means is nonconductive; and
    pulse generator means connected to said control means of said plurality of switch means for applying control signals to said control means upon said charge storage means reaching a predetermined level to thereby control the conductive state of each of said plurality of switch means to sequentially connect and disconnect said output potentials of said plurality of charge storage means to and from said first and second output terminal means in selected additive and subtractive combinations to generate a multiphasic defibrillation pulse waveform for application to the heart.

2. The apparatus of claim 1 further comprising:
    means responsive to the attainment by at least one of said plurality of charge storage means of a predetermined level of charge
    for disabling said charging means from further charging of said charge storage means; and
    means responsive to the attainment by said at least one of said plurality of charge storage means of said predetermined level of charge for enabling said pulse generator means to generate said multiphasic pulse waveform.

3. The apparatus of claim 2 wherein said means responsive to the attainment of a predetermined level of charge comprises:
    means for receiving signals indicative of said predetermined level of charge;
    means for producing from said signals a first scaled reference level;
    means for detecting the valve of charge stored in at least one of said charge storage means;
    means for producing from the detected level of charge a second scaled level indicative of said level of charge;
    means for comparing said second scaled level with said first scaled reference level; and
    means responsive to said means for comparing for disabling said charging means when aids second scaled level attains at least the level of said first scaled reference level.

4. The apparatus of claim 1 wherein said charging means comprises:
    charge generation means for generating an electrical charge during a charge generation cycle;
    charge coupling means for coupling said electrical charge to said charge storage means for storing said electrical charge during a subsequent charge coupling cycle; and
    detector means for detecting the end of each charge coupling cycle and initiating the next charge generation cycle.

5. The apparatus of claim 4 wherein said detector means comprises:
means for sensing the level of electrical charge generated during said charge generation cycle;
means for detecting when said electrical charge has been stored by said charge storage means; and
means responsive to said means for detecting for generating a signal indicating the end of the charge coupling cycle when said means for detecting detects that said electrical charge has been stored by said charge storage means.

6. The apparatus of claim 5 including switch means connected in circuit with said charge generation means, said switch means being responsive to said signal generated by said detector means to conduct current through said charge generation means thereby causing said charge generation means to generate said electrical charge during said charge generation cycle, and being responsive to the absence of said signal to prevent current from flowing through said charge generation means thereby causing said charge coupling means to couple the generated electrical charge to said charge storage means during said charge coupling cycle.

7. The apparatus of claim 1 wherein said pulse generator means includes
a plurality of driver means for generating said control signals.

8. The apparatus of claim 7 wherein each of said plurality of driver means is connected to the control means of a pair of said switch means connected in circuit between at least one of said charge storage means and said first sand second output terminals for simultaneously controlling the conduction states of both switch means of said pair to connect and disconnect the potential of said at least one charge storage means across said first and second output terminals.

9. The apparatus of claim 8 wherein:
said plurality of switch means comprises two pairs of switch means;
said plurality of charge storage means comprises a first charge storage means having a first output potential and a second charge storage means having a second output potential;
a first switch means from each pair are connected in a first series connection between said first output potential of said first charge storage means and said second output potential of said second charge storage means;
a second switch means from each pair are connected in a second series connection parallel to the first series connection between said first output potential of said first charge storage means and said second output potential of said second charge storage means;
said first output terminal adapted for connection to a heart comprises the junction of said first series connection between said first switch means from each pair; and said second output terminal adapted for connection to a heart comprises the junction of said second series connection between said second switch means from each pair.

10. The apparatus of claim 8 including protection means connected to said plurality of driver means disabling every other drive means of said plurality from turning its corresponding pair of switch means to the conductive state when any one of said driver means of said plurality is already enabled to turn its corresponding pair of said switch means to the conductive state.

11. A cardiac defibrillator, comprising:
first and second output terminal means for electrical connection to a heart;
a plurality of charge storage means forming a single multilevel source of waveforms, each storage means storing an electrical charge to provide an output potential;
low voltage power source means;
charging means connected to said plurality of charge storage means and said low voltage power source means for charging said charge storage means;
a plurality of switch means, each having control means operative to render the switch means conductive in response to a control signal, one said switch means of said plurality being connected in circuit between a respective one of each said charge storage means and each of said first and second output terminal means for connecting the potential provided by the said charge storage means to the respective terminal means when said switch means is conductive and disconnecting the potential provided by the said charge storage means from the respective terminal means when said switch means is non-conductive;
pulse generator means connected to said control means of said plurality of switch means for applying control signals to said control means to thereby connect and disconnect said output potentials of said plurality of charge storage means to and from said first and second output terminal means to and from said first and second output terminal means in selected additive and subtractive combinations to generate a multiphasic defibrillation pulse waveform for application to the heart;
means responsive to the onset of cardiac fibrillation for activating said charging means and;
means responsive to the attainment by at least one of said charge storage means of a predetermined level of charge sufficient to defibrillate the heart for activating said pulse generator means.

12. The apparatus of claim 11 wherein said charging means comprises:
charge generation means for generating electrical charge during a charge generation cycle;
charge coupling means for coupling said electrical charge to said charge storage means during a subsequent charge coupling cycle; and
detector means for detecting the end of each charge coupling cycle and initiating the next charge generation cycle.

13. The apparatus of claim 12 wherein said detector means comprises:
means for sensing the level of electrical charge generated during said charge generation cycle;
means for detecting when said electrical charge has been stored by said charge storage means; and
means responsive to said means for detecting for generating a signal indicating the end of the charge coupling cycle when said means for detecting detects that said electrical charge has been stored by said charge storage means.

14. The apparatus of claim 13 including switch means connected in circuit with said charge generation means, said switch means being responsive to said signal generated by said detector means to conduct current through said charge generation means thereby causing said charge generation means to generate said electrical charge during said charge generation cycle, and being responsive to the absence of said signal to prevent current from flowing through said charge generation means thereby causing said charge coupling means to couple the generated electrical charge to said charge storage means during said charge coupling cycle.

15. The defibrillator of claim 11 wherein said pulse generator means includes
a plurality of driver means for generating said control signals.

16. The defibrillator of claim 15 wherein each of said plurality of driver means is connected to the control means of a pair of said switch means connected in circuit between at least one of said charge storage means and said first and second output terminals for simultaneously controlling the conduction states of both switch means of said pair to connect and disconnect the potential of said at least one charge storage means across said first and second output terminals.

17. The defibrillator of claim 16 wherein:
said plurality of switch means comprises two pairs of switch means;
said plurality of charge storage means comprises a first charge storage means having a first output potential and a second charge storage means having a second output potential;
a first switch means from each pair are connected in a first series connection between said first output potential of said first charge storage means and said second output potential of said second charge storage means;
a second switch means from each pair are connected in a second series connection parallel to the first series connection between said first output potential of said first charge storage means and said second output potential of said second charge storage means; said first output terminal adapted for connection to a heart comprises the junction of said first series connection between said first switch means from each pair; and said second output terminal adapted for connection to a heart comprises the junction of said second series connection between said second switch means from each pair.

18. The defibrillator of claim 17 including protection means connected to said plurality of driver means and responsive to said control signals for automatically disabling every other driver means of said plurality from turning its corresponding pair of switch means to the conductive state when any one of said driver means of said plurality is already enabled to turn its corresponding pair of switch means to the conductive state.

19. An electrical stimulator apparatus, comprising:
first and second output terminal means for electrical connection to tissue to be stimulated;
a plurality of charge storage means forming a single multilevel source, each said storage means storing an electrical charge to provide an output potential;
low voltage power source means;
charging means connected to said plurality of charge storage means and said low voltage power source means for charging said charge storage means;
a plurality of switch means, each having control means operative to render the switch means conductive in response to a control signal, one switch means of said plurality being connected in circuit between a respective one of said charge storage means and each of said first and second output terminal means for connecting the potential provided by the said charge storage means to the respective terminal means when said switch means is conductive and disconnecting the potential provided by the said charge storage means from the respective terminal means when said switch means is non-conductive;
pulse generator means connected to said control means of said plurality of switch means for applying control signals to said control means to thereby connect and disconnect said output potentials of said plurality of charge storage means to and from said first and second output terminal means in selected additive and subtractive combinations to generate a multiphasic pulse waveform for application to said tissue to be stimulated and
lead means connected between said first and second output terminal means and the tissue to be stimulated.

20. The stimulator apparatus of claim 19, including:
means responsive to a predetermined physiological condition for enabling said charging means to charge said charge storage means; and
means responsive to the attainment by at least one of said charge storage means of a predetermined level of charge for enabling said pulse generator means to generate said multiphasic pulse waveform .

21. A cardiac defibrillator, comprising:
a single source having a plurality of storage means for storing multilevel electrical charges; means responsive to onset of fibrillation for initiating charging of said storing means;
means for detecting the level of charge stored by said storing means to interrupt said charge upon attainment of a preselected level of stored charge; and
means responsive to attainment of said preselected level for sequentially discharging said storing means with successive alternations of polarity over selected time intervals to generate a multiphasic pulse waveform having at least two successive electrical pulses of predetermined magnitude, duration, and opposite polarity sequence, with energy content sufficient for defibrillation, for delivery to the patient's heart.

22. The defibrillator of claim 21, wherein said discharging means includes means for selecting the polarity with which said storing means is first discharged upon attainment of said preselected level, to establish the sequence of alternating polarity of the pulses in said waveform.

23. The defibrillator of claim 21, further including means for setting said time intervals to establish the duration of each pulse in said waveform.

24. The defibrillator of claim 21, further including means for setting said preselected level of charge to establish the initial magnitude of the first pulse in said waveform.

25. The defibrillator of claim 24, further including means for setting said time intervals and the separation thereof, to establish the duration of each pulse, and the initial magnitude of each pulse following the first pulse, in said waveform.

26. The defibrillator of claim 21, wherein said charging means includes means for cyclically delivering packets of electrical charge to said storing means, each packet having a predetermined magnitude, until attainment of said preselected level.

27. The defibrillator of claim 21, further including conductive lead means for connection at one end thereof to said discharging means and including electrode means at the other end thereof for making electrically stimulating relationship to the patient's heart, to deliver said waveform to the heart.

28. The defibrillator of claim 21, wherein said storing means includes a pair of series-connected high-voltage charge-storing capacitors, said charging means includes means for cyclically delivering electrical charge in packets, each of predetermined magnitude, to the charge-storing capacitors until said preselected level of charge is attained, and said discharging means includes means for generating said waveform by sequential discharge of the capacitors to provide the sequence of pulses of successively opposite polarity.

29. The defibrillator of claim 28, wherein said generating means partially discharges the charge stored on both capacitors in first one polarity and then the opposite polarity.

30. The defibrillator of claim 28, wherein said generating means partially discharges the charge stored on only one of said capacitors in one polarity and then discharges the charge stored on the other capacitor and the remaining charge stored on said one capacitor in the opposite polarity.

* * * * *